US006974801B2

(12) United States Patent
Honda et al.

(10) Patent No.: US 6,974,801 B2
(45) Date of Patent: Dec. 13, 2005

(54) INHIBITORS AND METHODS OF USE THEREOF

(75) Inventors: Tadashi Honda, Hanover, NH (US); Yukiko Honda, Hanover, NH (US); Gordon W. Gribble, Lebanon, NH (US); Michael B. Sporn, Tunbridge, VT (US); Nanjoo Suh, White River Junction, VT (US)

(73) Assignee: The Trustees of Dartmounth College, Hanover, NH (US)

( * ) Notice: Subject to any disclaimer, the term of this patent is extended or adjusted under 35 U.S.C. 154(b) by 0 days.

(21) Appl. No.: 10/435,925

(22) Filed: May 12, 2003

(65) Prior Publication Data

US 2004/0002463 A1 Jan. 1, 2004

Related U.S. Application Data

(60) Provisional application No. 60/378,009, filed on May 13, 2002.

(51) Int. Cl.[7] .................... A61K 31/70; A61K 31/4164; C07H 13/08

(52) U.S. Cl. .................... 514/25; 514/396; 514/359; 514/383; 514/463; 536/4.1; 548/266.8; 548/304.4; 548/334.1

(58) Field of Search .................... 514/25, 396, 359, 514/383, 463; 536/4.1; 548/266.8, 304.4, 334.1

(56) References Cited

U.S. PATENT DOCUMENTS

| 5,064,823 A | 11/1991 | Lee et al. .................... 514/198 |
| 6,326,507 B1 * | 12/2001 | Gribble et al. ............... 558/415 |
| 2002/0042535 A1 | 4/2002 | Gribble et al. ............... 558/429 |

OTHER PUBLICATIONS

Honda et al. (Bioorganic & Medicinal chemistry Letters 12 (2002) 1027–1030).*
Kircher, "Triterpenes, in organ pipe cactus," *Phytochemistry*, 19:2707–2712, 1980; Dataase CAPPLUS on STN AN:1981:550946.
Takabe et al., "Synthesis of lycosyl esters of oleanolic," *Cqrbohydrate Research*, 76:101–108, 1979, Dataase CAPPLUS on STN AN:1980:42278.
Ambs et al., "p53 and vascular endothelial growth factor regulate tumor growth of NOS2–expressing human carcinoma cells," *Nat. Med.*, 4(12):1371–1376, 1998.
Bliard et al., "Glycosylation of acids under phase transfer conditions. Partial synthesis of saponins," *Tetrahedron Lett.*, 35:6107–6108, 1994.
Bogdon and Ding, "Taxol, a microtubule–stabilizing antineoplastic agent, induces expression of tumor necrosis factor α and interleukin–1 in macrophages," *J. Leukoc. Biol.*, 52(1):119–121, 1992.

Boolbol et al., "Cyclooxygenase–2 overexpression and tumor formation are blocked by sulindac in a murine model of familial adenomatous polyposis," *Cancer Res.*, 56(11):2556–2560, 1996.
Ding et al., "Macrophage deactivating factor and transforming growth factors–$\beta_1$, –$\beta_2$ and –B$_3$ inhibit induction of macrophage nitrogen oxide synthesis by IFN–$\gamma^1$," *J Immunol.*, 145(3):940–944, 1990.
Drefahl and Huneck, "Nor–olea–12–enol–17–amin und Olea–12–enol–28–amin," *Chem. Ber.*, 91:278–281, 1958.
DuBois et al., "Increased cyclooxygenase–2 levels in carcinogen–induced rat colonic tumors," *Gastroenterology*, 110:1259–1262, 1996.
Honda et al., "A novel dicyanotriterpenoid, 2–cyano–3,12–dioxooleanan–1,9(11)–dien–28–onitrile, active at picomolar concentrations for inhibition of nitric oxide production," *Bioorganic & Medicinal Chemistry Letters*, 12:1027–1030, 2002.
Honda et al., "Design and synthesis of 2–cyano–3,12–dioxoolean–1,9–deien–28–oic acid, a novel and highly active inhibitor of nitric oxide production in mouse macrophages," *Bioorg. Med. Chem. Lett.*, 8:2711–2714, 1998.
Honda et al., "New enone derivatives of oleanolic acid and ursolic acid as inhibitors of nitric oxide procution in mouse macrophages," *Bioorg. Med. Chem. Lett.*, 7:1623–1628, 1997.
Honda et al., "Novel synthetic oleanane and ursane triterpenoids with various enone functionalities in ring A as inhibitors of nitric oxide production in mouse macrophages, "*J. Med. Chem.*, 43:1866–1877, 2000.
Honda et al., "Novel synthetic oleanane triterpenoids: a series of highly active inhibitors of nitric oxide production in mouse macrophages," *Bioorg. Med. Chem. Lett.*, 9:3429–3434, 1999.

(Continued)

*Primary Examiner*—Elvis O. Price
*Assistant Examiner*—Michael C. Henry
(74) *Attorney, Agent, or Firm*—Fulbright & Jaworski

(57) ABSTRACT

New triterpenoid derivatives with various substituents at the C–17 position of 2-cyano-3,12-dioxooleana-1,9(11)-dien-28-oic acid (CDDO) were synthesized. Among them, 2-cyano-3,12-dioxooleana-1,9(11)-dien-28-onitrile (CNDDO), 1-(2-cyano-3,12-dioxooleana-1,9(11)-dien-28-oyl) imidazole, 1-(2-cyano-3,12-dioxooleana-1,9(11)-dien-28-oyl)-2-methylimidazole, 1-(2-cyano-3,12-dioxooleana-1,9(11)-dien-28-oyl)-4-methylimidazole show extremely high inhibitory activity ($IC_{50}$=0.01–1 pM level) against production of nitric oxide induced by interferon-$\gamma$ in mouse macrophages. These compounds can be used in the prevention or treatment of diseases such as cancer, Alzheimer's disease, Parkinson's disease, multiple sclerosis, rheumatoid arthritis, and other inflammatory diseases. All the new triterpenoid derivatives are more potent than previously known CDDO.

18 Claims, No Drawings

OTHER PUBLICATIONS

Honda et al., "Synthetic oleanane and ursane triterpenoids with modified rings A and C: a series of highly active inhibitors of nitric oxide production in mouse macrophages," *J. Med. Chem.*, 43:4233–4246, 2000.

Huang et al., "Inhibition of skin tumorigenesis by Rosemary and its constituents carnosol and ursolic acid," *Cancer Res.*, 54:701–708, 1994.

Kawamori et al., "Chemopreventive activity of celecoxib, as specific cyclooxygenase–2 inhibitor, against colon carcinogenesis," *Cancer Res.*, 58(3):409–412, 1998.

Lemieux, "Acylglycosyl Halides. [55] tetra–O–acetyl–α–D–glucopyranosyl bromide," *Methods Carbohydr. Chem.*, 2:221–222, 1963.

Marnett, "Aspirin and the potential role of prostaglandins in colon cancer," *Cancer Res.*, 52(20):5575–5589, 1992.

Moncada et al., "Nitric oxide: physiology, pathophysiology, and pharmacology," *Pharmacol. Rev.*, 43:109–142, 1991.

Nathan and Xie, "Nitric oxide synthases: roles, tolls, and controls," *Cell*, 78:915–918, 1994.

Nishino et al., "Inhibition of the tumor–promoting action of 12–O tetradecanoylphorbol–13–acetate by some oleanane–type triterpenoid compounds," *Cancer Res.*, 48:5210–5215, 1988.

Ohshima and Bartsch, "Chronic infections and inflammatory process as cancer risk factors: possible role of nitric oxide in carcinogenesis," *Mutat. Res.*, 305:253–264, 1994.

Ono et al., "A convenient procedure for esterification of carboxylic acids," *Bull. Chem. Soc. Jpn.*, 51:2401–2404, 1978.

Oshima et al., "Suppression of intestinal polyposis in $Apc^{\Delta 716}$ knockout mice by inhibition of cyclooxygenase 2 (COX–2)," *Cell*, 87:803–809, 1996.

Prescott and White, "Self–promotion? Intimate connections between APC and prostaglandin H synthase–2," *Cell*, 87:783–786, 1996.

Reddy et al., "Evaluation of cyclooxygenase–2 inhibitor for potential chemopreventive properties in colon carcinogenesis," *Cancer Res.*, 56(20):4566–4569, 1996.

Salvemini et al., "Endogenous nitric oxide enhances prostaglandin production in a model of renal inflammation," *J. Clin. Invest.*, 93(5):1940–1947, 1994.

Salvemini et al., "Nitric oxide activates cyclooxygenase enzymes," *Proc. Natl. Acad. Sci. USA*, 90(15):7240–7244, 1993.

Seibert and Masferrer, "Role of inducible cyclooxygenase (COX–2) in inflammation," *Receptor*, 4(1):17–23, 1994.

Sheng et al., "Inhibition of human colon cancer cell growth by selective inhibition of cyclooxygenase–2," *J. Clin. Invest.*, 99(9):2254–2259, 1997.

Sporn and Roberts, "Peptide growth factors and inflammation, tissue repair, and cancer," *J. Clin. Invest.*, 78:329–332, 1986.

Suh et al., "A novel synthetic oleanane triterpenoid, 2–cyano–3,12–dioxoolean–1,9–dien–28–oic acid, with potent differentiating, antiproliferative and anti–inflammatory activity," *Cancer Res.*, 59:336–341, 1999.

Suh et al., "Novel triterpenoids suppress inducible nitric oxide synthase (iNOS) and inducible cyclooxygenase (COX–2) in mouse macrophages," *Cancer Res.*, 58:717–723, 1998.

Takahashi et al., "Increased expression of inducible and endothelial constitutive nitric oxide synthases in rat colon tumors induced by azoxymethane," *Cancer Res.*, 57:1233–1237, 1997.

Tamir and Tannebaum, "The role of nitric oxide (NO) in the carcinogenic process," *Biochim. Biophys. Acta*, 1288:F31–F36, 1996.

Tsujii and DuBois, "Alterations in cellular adhesion and apoptosis is epithelial cells overexpressing prostaglandin endoperoxide synthase 2," *Cell*, 83:493–501, 1995.

Tsujii et al., "Cyclooxygenases regulates angiogenesis induced by colon cancer cells," *Cell*, 93:705–716, 1998.

Wang et al., "A synthetic triterpenoid, 2–cyano–3,12–dioxooleana–1,9–dien–28–oic acid (CDDO), is a ligand for the peroxisome proliferator–activated receptor γ," *Mol. Endocrinol.*, 14:1550–1556, 2000.

\* cited by examiner

INHIBITORS AND METHODS OF USE THEREOF

The present application claims the priority of provisional U.S. Ser. No. 60/378,009, filed May 13, 2002, the entire contents of which are incorporated herein by reference and without disclaimer.

The present invention disclosed herein was made with the support of the U.S. Government under NIH Grant 1R01-CA78814, U.S. Department of Defense Grants DAMD 17-96-1-6163, DAMD 17-98-1-8604, and DAMD 17-99-1-9168. Accordingly, the U.S. Government may have certain rights in this invention.

BACKGROUND OF THE INVENTION

I. Field of the Invention

The present invention provides triterpenoid derivatives, as well as processes for the preparation of such derivatives. The invention also provides methods for prevention and/or treatment of cancer, Alzheimer's disease, Parkinson's disease, multiple sclerosis, amyotropic lateral sclerosis, rheumatoid arthritis, inflammatory bowel disease, and all other diseases whose pathogenesis is believed to involve excessive production of either nitric oxide (NO) or prostaglandins.

II. Description of Related Art

One of the major needs in cancer prevention is the development of effective and safe new agents for chemoprevention. In particular, there is a need for chemopreventative agents targeted at mechanisms known to be involved in the process of carcinogenesis. In recent years, there has been a resurgence of interest in the study of mechanisms of inflammation that relate to carcinogenesis and in the use of such mechanisms as the basis for development of new chemopreventative agents.

The concept that inflammation and carcinogenesis are related phenomena has been the subject of many studies that have attempted to link these two processes in a mechanistic fashion (Sporn and Roberts, 1986; Ohshima and Bartsch, 1994). The enzymes that mediate the constitutive synthesis of NO and prostaglandins from arginine and arachidonate, respectively, have relative little significance for either inflammation or carcinogenesis. In contrast, inducible nitric oxide synthase (iNOS) and inducible cycloxygenase (COX-2) both have critical roles in the response of tissues to injury or infectious agents (Moncada et al., 1991; Nathan and Xie, 1994; Siebert and Masferrer, 1994; Tamir and Tannebaum, 1996). These inducible enzymes are essential components of the inflammatory process, the ultimate repair of injury, and carcinogenesis. While physiological activity of iNOS and COX-2 may provide a definite benefit to the organism, aberrant or excessive expression of either iNOS or COX-2 has been implicated in the pathogenesis of many disease processes, particularly in chronic degeneration of the central nervous system, carcinogenesis, septic shock, cardiomyopathy, and rheumatoid arthritis.

Triterpenoids, biosynthesized in plants by the cyclization of squalene, are used for medicinal purposes in many Asian countries; and some, like ursolic and oleanolic acids, are known to be anti-inflammatory and anti-carcinogenic (Huang et al., 1994; Nishino et al., 1988). However, the biological activity of these naturally occurring molecules is relatively weak, and therefore the synthesis of new analogs to enhance their potency was undertaken (Honda et al., 1997; Honda et al., 1998). It was previously reported that several such synthetic analogs can suppress the de novo formation of iNOS and COX-2 in macrophages that have been stimulated by IFN-γ or LPS (Suh et al., 1998). The role of both iNOS and COX-2 as enhancers of carcinogenesis in many organs is receiving increasing attention (Ohshima et al., 1994; Tamir et al., 1996; Takahashi et al., 1997; Ambs et al., 1998; Tsujii et al., 1998; Oshima et al., 1996); suppression of either the synthesis or the activity of these enzymes is therefore a target for chemoprevention (Kawamori et al., 1998). Agents which induce differentiation or suppress proliferation of premalignant or malignant cells represent yet another mechanistic approach to chemoprevention, as well as to chemotherapy, of cancer.

The present inventors have previously reported that 2-cyano-3,12-dioxooleana-1,9(11)-dien-28-oic acid (CDDO) (Table 1), its methyl ester and methyl 2-carboxy-3,12-dioxooleana-1,9(11)-dien-28-oate show high inhibitor activity against production of nitric oxide (NO) induced by interferon-γ in mouse macrophages ($IC_{50}$=0.1 nM level) (Honda et al., 1998; Honda et al., 1999; Honda et al., 2000a; Honda et al., 2000b). The inventors also reported that CDDO is a potent, multifunctional agent in various in vitro assays (Suh et al., 1999). For example, CDDO induces monocytic differentiation of human myeloid leukemia cells and adipogenic differentiation of mouse 3T3-L1 fibroblasts. CDDO also inhibits proliferation of many human tumor cell lines, and blocks de novo synthesis of inducible nitric oxide synthase (iNOS) and inducible cyclooxygenase (COX-2) in mouse macrophases. The above potencies have been found at concentrations ranging from $10^{-6}$ to $10^{-9}$ M in cell culture. Mechanism studies revealed that CDDO is a ligand for peroxisome proliferator-activated receptor γ (PPARγ) (Wang et al., 2000) and induces apoptosis in human myeloid leukemia cells.

However, it would be advantageous to develop compounds exhibiting higher inhibitory activity against the production of nitric oxide induced by interferon-γ in mouse macrophages. The availability of compounds having potency higher than that of CDDO is important for the prevention or treatment of diseases such as cancer, Alzheimer's disease, Parkinson's disease, and multiple sclerosis.

SUMMARY OF THE INVENTION

The present invention provides methods and compositions for the prevention or treatment of diseases such as cancer, Alzheimer's disease, Parkinson's disease, and multiple sclerosis. Thus, in accordance with the present invention, there is provided a compound having the formula:

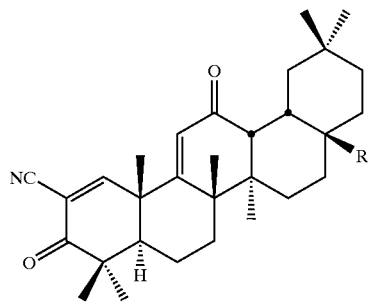

wherein R is CN, CO-D-Glu(OAc)$_4$, CONH$_2$, CONHNH$_2$,

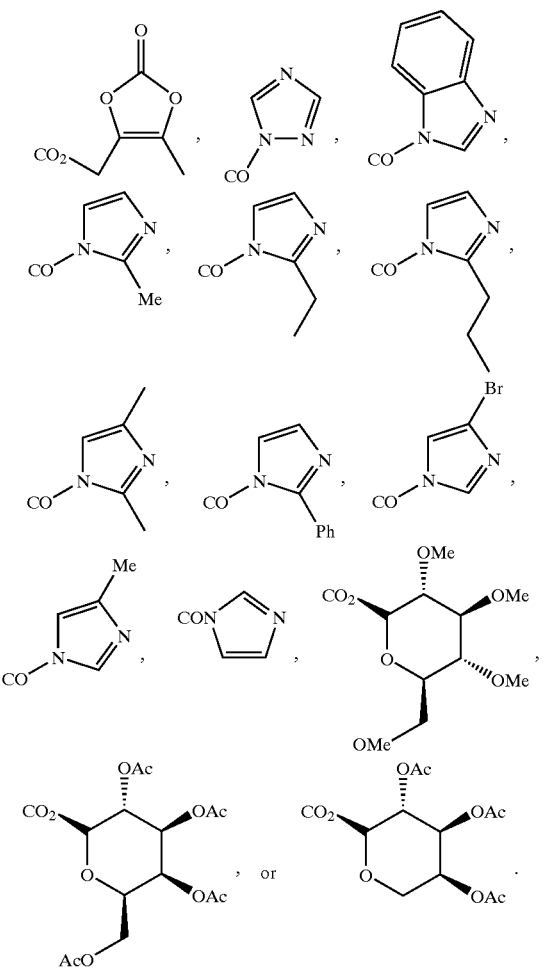
Thus, in some specific embodiments, the invention provides compounds of the formula:
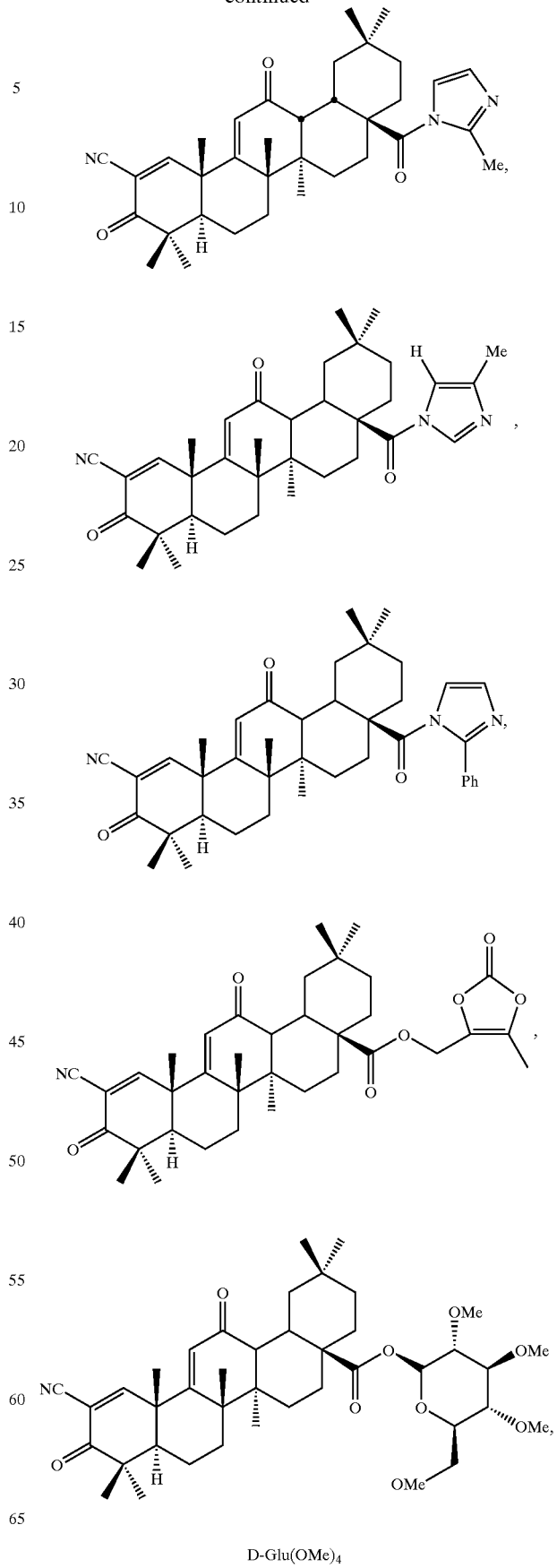

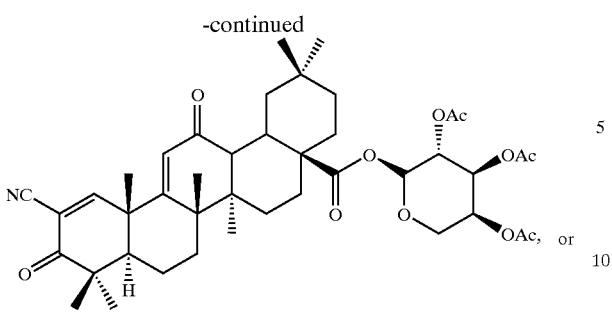

L-Ara(OAc)₃

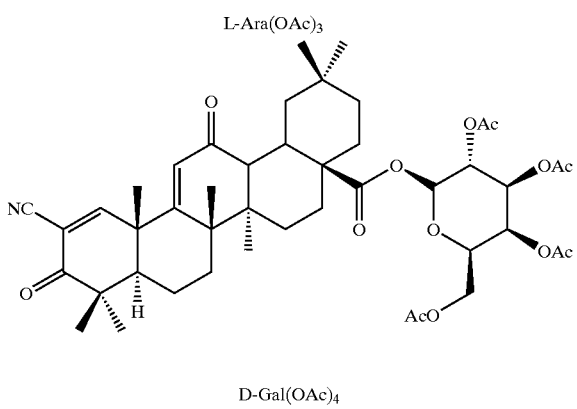

D-Gal(OAc)₄ as well as isomers thereof.

Also provided are methods of treating a subject or a patient comprising administering a therapeutically effective amount of one or more of the compounds set forth above. In one embodiment, the disease states that the patient may be afflicted with include cancer, such as cancer of the brain, lung, liver, spleen, kidney, lymph node, small intestine, pancreas, blood cell, bone, colon, stomach, bread, endometrium, prostate, testicle, ovary, central nervous system, skin, head and neck, esophagus, or bone marrow. In some embodiments of the invention, the patient may only be at risk for the development of cancer, and the treatment is prophylactic.

In other embodiments, the disease may be an inflammatory disease, such as rheumatoid arthritis or inflammatory bowel disease. In yet other embodiments, the disease may be a neurodegenerative disease, such as Alzheimer's disease, Parkinson's disease, multiple sclerosis or amyotrophic lateral sclerosis. In still other embodiments, the patient may have a pathogenesis involving the excessive production of nitric oxide or prostaglandins.

Also provided are:

methods for preventing or treating a disorder characterized by the overexpression of iNOS or COX-2 genes comprising administering to a subject or a patient a pharmaceutically effective amount of a composition containing a compound described above;

methods of modulating transcription or translation of iNOS or COX-2 genes in a patient comprising administering to a subject or a patient a pharmaceutically effective amount of a composition containing a compound described above; and methods of modulating excessive nitric oxide or prostaglandin formation in a patient comprising administering to a subject or a patient a pharmaceutically effective amount of a composition containing a compound described above.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Before further description of the invention, certain terms employed in the specification, examples and appended claims are, for convenience, collected here.

I. Definitions

As used herein, the term "organic moiety" is intended to include carbon based functional groups such as alkyl, alkylamino, alkoxy, aryl, aralkyl, aryloxy, alkylthio, and alkylcarboxyl.

As used herein, the term "inorganic moiety" is intended to include non carbon-based groups or elements such as hydrogen, halo, amino, nitro, thiol, and hydroxyl.

As used herein, the term "electron withdrawing moiety" is known in the art, and refers to a group which has a greater electron-withdrawing than hydrogen. A variety of electron-withdrawing groups are known, and include halogens (e.g., fluoro, chloro, bromo, and iodo groups), nitro, cyano, $-NR_3^+$, $-SR_2^+$, $-NH_3^+$, $-SO_2R$, $-SO_2Ar$, $-COOH$, $-OAr$, $-COOR$, $-OR$, $-COR$, $-SH$, $-SR$, $-OH$, $-Ar$, and $-CH=CR_2$, where Ar is aryl, and R represents any appropriate organic or inorganic moiety and, preferably, alkyl moiety.

As used herein, the term "halosubstituted alkyl moieties" is intended to include alkyl moieties which have halogen moieties in the place of at least one hydrogen.

As used herein, the term "amino" means $-NH_2$; the term "nitro" means $-NO_2$; the term "halogen" designates $-F$, $-Cl$, $-Br$ or $-I$; the term "thiol" means SH; and the term "hydroxyl" means $-OH$. Thus, the term "alkylamino" as used herein means an alkyl group, as defined above, having an amino group attached thereto. The term "alkylthio" refers to an alkyl group, as defined above, having a sulfhydryl group attached thereto. The term "alkylcarboxyl" as used herein means an alkyl group, as defined above, having a carboxyl group attached thereto.

The term "aromatic group" is intended to include unsaturated cyclic hydrocarbons containing one or more rings. Aromatic groups include 5- and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. The aromatic ring may be substituted at one or more ring positions with, for example, a halogen, a lower alkyl, a lower alkenyl, a lower alkoxy, a lower alkylthio, a lower alkylamino, a lower alkylcarbonyl, a nitro, a hydroxyl, $-CF3$, $-CN$, or the like.

The term "alkyl" refers to the saturated aliphatic groups, including straight-chain alkyl groups, branched-chain alkyl groups, cycloalkyl (alicyclic) groups, alkyl substituted cycloalkyl groups, and cycloalkyl substituted alkyl groups.

Moreover, the term "alkyl" (including "lower alkyl") as used throughout the specification and claims is intended to include both "unsubstituted alkyls" and "substituted alkyls", the latter of which refers to alkyl moieties having moieties replacing a hydrogen on one or more carbons of the hydrocarbon backbone. Such moieties can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the moieties described above. An "aralkyl" moiety is an alkyl substituted with an aryl (e.g., phenylmethyl (benzyl)).

The term "alkoxy", as used herein, refers to a moiety having the structure —O-alkyl, in which the alkyl moiety is described above.

The term "aryl" as used herein includes 5- and 6-membered single-ring aromatic groups that may include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. The aromatic ring can be substituted at one or more ring positions with such moieties, e.g., as described above for alkyl groups. Preferred aryl groups include unsubstituted and substituted phenyl groups.

The term "aryloxy", as used herein, refers to a group having the structure —O-aryl, in which the aryl moiety is as defined above.

The term "amino," as used herein, refers to an unsubstituted or substituted moiety of the formula —$NR_aR_b$, in which $R_a$ and $R_b$ are each independently hydrogen, alkyl, aryl, or heterocyclic, or $R_a$ and $R_b$, taken together with the nitrogen atom to which they are attached, form a cyclic moiety having from 3 to 8 atoms in the ring. Thus, the term "amino" is intended to include cyclic amino moieties such as piperidinyl or pyrrolidinyl groups, unless otherwise stated. An "amino-substituted amino group" refers to an amino group in which at least one of $R_a$ and $R_b$, is further substituted with an amino group.

As used herein, the term "subject" or "patient" is intended to include living organisms in which certain conditions as described herein can occur. Examples include humans, monkeys, cows, sheep, goats, dogs, cats, mice, rats, and transgenic species thereof. In a preferred embodiment, the subject is a primate. In an even more preferred embodiment, the primate is a human. Other examples of subjects include experimental animals such as mice, rats, dogs, cats, goats, sheep, pigs, and cows. The experimental animal can be an animal model for a disorder, e.g., a transgenic mouse with an Alzheimer's-type neuropathology. A subject can be a human suffering from a neurodegenerative disease, such as Alzheimer's disease, or Parkinson's disease.

As used herein, the term "$IC_{50}$" refers to an inhibitory dose which is 50% of the maximum-response obtained.

Other abbreviations used herein are as follows: CDDO, 2-cyano-3,12-dioxoolean-1,9-dien-28-oic acid; 2-cyano-3, 12-dioxooleana-1,9(11)-dien-28-onitrile (CNDDO), DMSO, dimethyl sulfoxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFN-γ, interferon-γ; LPS, bacterial endotoxic lipopolysaccharide; TNF-α, tumor necrosis factor-α; IL-1β, interleukin-1β; GAPDH, glyceraldehyde-3-phosphate dehydrogenase; MTT, 3-[4,5-dimethylthiazol-2-yl]-2,5-diphenyltetrazolium bromide; TCA, trichloroacetic acid.

II. Administration

The compounds of the invention may be administered by a variety of methods, e.g., orally or by subcutaneous, intravenous, intraperitoneal, etc. administration (e.g., by injection). Depending on the route of administration, the active compound may be coated in a material to protect the compound from the action of acids and other natural conditions which may inactivate the compound.

To administer the therapeutic compound by other than parenteral administration, it may be necessary to coat the compound with, or co-administer the compound with, a material to prevent its inactivation. For example, the therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., (1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilated edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a subject.

Active compounds are administered at a therapeutically effective dosage sufficient to treat a condition associated with a condition in a subject. A "therapeutically effective dosage" preferably reduces the amount of symptoms of the condition in the infected subject by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans, such as the model systems shown in U.S. Pat. No. 6,326, 507.

III. Chemistry

Triterpenoids, like the steroids, are formed in nature by the cyclization of squalene, with the retention of all 30 carbon atoms in molecules such as ursolic acid (UA) and oleanoic acid (OA). Although OA and UA are known to have numerous pharmacological activities, the potency of these naturally occurring molecules is relatively weak. Triterpenoid derivatives such as CDDO were discovered to have a higher potency than either OA or UA (U.S. Pat. No. 6,326, 507) (Table 1).

The current invention encompasses various triterpenoid derivatives with varying substituent groups (i.e., cyano, substituted and unsubstituted carbonyl imidazoles, esters, glycosides, and amides) at C-17 with all derivatives exhibiting a higher potency than CDDO (see Tables 1–3).

These compounds and derivatives thereof are useful in prevention treatment methodology or treatment of diseases such as cancer, Alzheimer's disease, Parkinson's disease, multiple sclerosis, rheumatoid arthritis, and other inflammatory diseases.

The preferred embodiments of the current invention are 2-cyano-3,12-dioxooleana-1,9(11)-dien-28-onitrile (CNDDO), 1-(2-cyano-3,12-dioxooleana-1,9(11)-dien-28-oyl)imidazole, 1-(2-cyano-3,12-dioxooleana-1,9(11)-dien-28-oyl)-2-methylimidazole, and 1-(2-cyano-3,12-dioxooleana-1,9(11)-dien-28-oyl)-4-methylimidazole all of which show extremely high inhibitory activity ($IC_{50}=0.01-1$ pM level) against production of nitric oxide induced by interferon-$\gamma$ in mouse macrophages. In other preferred embodiments the invention provides D-Glu(OMe)$_4$, L-Ara (OAc)$_3$, and D-Gal(OAc)$_4$. The synthesis, inhibitory activity and structure-activity relationships (SAR) of the aforementioned and other new analogues is described herein.

The preferred compounds with modifications at C-17 can be described based on SAR results for the inhibitory activities [$IC_{50}$ (nM) value] of compounds 1–18 on NO production induced by IFN-$\gamma$ in mouse macrophages (Tables 1–3). These results provide the following SAR about substituents at C-17:

(1) A nitrile group enhances potency. Dinitrile 1 is much more potent than 4, 5 ,7 and CDDO (Table 1).

(2) Protected glycoside 2, and 16–18 are more potent than CDDO (Tables 1 and 3).

(3) Amide moieties follow the trend that the less polar the amide, the less is its potency. Accordingly, amide 3 and hydrazide 4 show greater potency than CDDO (Table 1).

(4) Carbonyl imidazoles 6–15 all exhibit higher potency than CDDO with compound 10 showing the greatest potency (Tables 1 and 2).

Some of the compounds had good in vivo anti-inflammatory activity, when given i.p. or p.o., against peritoneal inflammation induced by thioglycollate and IFN-$\gamma$.

IV. Uses

Compounds described herein have utility for prevention and treatment of cancer, Alzheimer's disease (AD), Parkinson's disease (PD), multiple sclerosis (MS), amyotrophicleteral sclerosis (ACS), rheumatoid arthritis (RA), inflammatory bowel disease, and all other diseases whose pathogenesis is believed to involve excessive production of either nitric oxide or prostaglandins.

The aberrant or excessive expression of either iNOS or COX-2 has been implicated in the pathogenesis of many disease processes, including carcinogenesis in the colon. Thus, overexpression of the gene for COX-2 is an early and central event in colon carcinogenesis (Prescott and White, 1996; Dubois et al., 1996). Mice with defects in the APC (adenomatous polyposis coli) gene develop large numbers of intestinal polyps at an early age, and marked elevations in COX-2 enzyme levels have been found in these polyps. These animal findings correlate with the finding of elevated levels of COX-2 mRNA and protein in many human primary colon cancers and colon cancer cell lines (Prescott and White, 1996), and it is believed that this elevation in COX-2 leads to a suppression of apoptosis, which would ordinarily lead to death of preneoplastic cells (Tsujii and DuBois, 1995). The functional relevance of COX-2 to intestinal tumorigenesis has been demonstrated by knockout of the COX-2 gene and the subsequent mating of mice bearing this knockout with polyp-forming mice bearing lesions in the APC gene; the COX-2 knockout caused a dramatic diminution in the number of polyps in the offspring (Oshima et al., 1996). Furthermore, treatment of experimental animals with either selective COX-2 inhibitors or non-selective COX-1/COX-2 inhibitors has been reported to be a potent approach to chemoprevention of intestinal cancer (Mamett, 1992; Oshima et al., 1996; Boolbol et al., 1996; Reddy et al., 1996; Sheng et al., 1997). As for the role of iNOS in carcinogenesis, it is clear that NO is a potent mutagen (Tamir and Tannebaum, 1996), and that nitric oxide can also activate COX-2 (Salvemini et al., 1993, 1994). Furthermore, there is a marked increase in iNOS in colon tumors induced by the carcinogen, azoxymethane (Takahashi et al., 1997).

MS is known to be an inflammatory condition of the central nervous system (Williams et al., 1994; Merrill and Beneviste, 1996; Genain and Hauser, 1997). Inflammatory, oxidative, or immune mechanisms may be involved in the pathogenesis of MS, AD, PD, and ALS (Bagasra et al., 1995; McGeer and McGeer, 1995; Simonian and Coyle, 1996). Both reactive astrocytes and activated microglia have been implicated in causation of NDD/NID; there has been a particular emphasis on microglia as cells that synthesize both NO and prostaglandins as products of the respective enzymes, iNOS and COX-2. De novo formation of these enzymes may be driven by inflammatory cytokines such as interferon-gamma or interleukin-1. In turn, excessive production of NO may lead to inflammatory cascades and/or oxidative damage in cells and tissues of many organs, including neurons and oligodendrocytes of the nervous system, with consequent manifestations in AD and MS, and possible PD and ALS (Coyle and Puttfarcken, 1993; Beal, 1996; Merrill and Benvenist, 1996; Simonian and Coyle, 1996; Vodovotz et al., 1996). Epidemiologic data indicate that chronic use of NSAID's which block synthesis of prostaglandins from arachidonate, markedly lower the risk for development of AD (McGeer et al., 1996; Stewart et al., 1997). Thus, agents that block formation of NO and prostaglandins, may be used in approaches to prevention and treatment of NDD.

The triterpenoid derivatives described herein have three important properties: 1) they are potent agents for induction of differentiation in both malignant and non-malignant cells; 2) they are active at nanomolar levels as an inhibitor of proliferation of many malignant or premalignant cells; and 3) they are thousands-fold more potent than most previous triterpenoid in suppressing the de novo synthesis of the inflammatory enzymes, iNOS and COX-2 and are up to 100 and 30 times more potent than CDDO and dexamethasone respectively. These three actions are important for the development of a useful new chemopreventive agent, and they are also relevant to therapy of malignancy itself as well.

The practice of the present invention will employ, unless otherwise indicated, conventional techniques of cell biology, cell culture, molecular biology, microbiology, recombinant DNA, and immunology, which are within the skill of the art. Such techniques are explained fully in the literature. (See, for example, Sambrook et al. 2001).

The invention is further illustrated by the following examples which should not be construed as further limiting the subject invention. The contents of all references, issued patents, and published patent applications cited throughout this application including the background are hereby incorporated by reference. A demonstration of efficacy of the therapeutic compounds of the present invention in the model(s) described in the Examples is predictive of efficacy in humans.

V. Combination Therapy

In addition to being used as a monotherapy, the therapeutic methods of the present invention will also find use in combination therapies. Such combination therapies may include the use of anti-inflammatory agents generally, or inhibitors of COX-2 and/or iNOS. Alternatively, the combination may be include a second anti-cancer therapy, as discussed in detail below.

An "anti-cancer" agent is capable of negatively affecting cancer in a patient, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the triterpenoid derivatives and the other agent(s) at the same time. This may be achieved by contacting the cell with a single composition or pharmacological formulation that includes both agents, or by contacting the cell with two distinct compositions or formulations, at the same time, wherein one composition includes the triterpenoid derivatives and the other includes the second agent(s).

Alternatively, the triterpenoid derivatives therapy may precede or follow the other agent treatment by intervals ranging from minutes to weeks. In embodiments where the other agent and triterpenoid derivative(s) are applied separately to the cell, one would generally ensure that a significant period of time did not expire between the time of each delivery, such that the agent and the triterpenoid derivatives would still be able to exert an advantageously combined effect on the cell. In such instances, it is contemplated that one may contact the cell with both modalities within about 12–24 h of each other and, more preferably, within about 6–12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed as set forth below where the triterpenoid derivative therapy is "A" and the secondary agent, is "B":

A/B/A B/A/B B/B/A A/A/B A/B/B B/A/A A/B/B/B

B/A/B/B B/B/B/A B/B/A/B A/A/B/B A/B/A/B A/B/B/A

B/B/A/A B/A/B/A B/A/A/B A/A/A/B B/A/A/A A/B/A/A

A/A/B/A

Other combinations are also contemplated. Administration of the triterpenoid derivative compounds of the present invention to a patient will follow general protocols for the administration of chemotherapeutics, taking into account the toxicity, if any, of the drug. It is expected that the treatment cycles would be repeated as necessary. It also is contemplated that various standard therapies, as well as surgical intervention, may be applied in combination with the triterpenoid derivatives of the invention.

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that triterpenoid derivative therapy could be used similarly in conjunction with chemotherapeutic, radiotherapeutic, or immunotherapeutic intervention, in addition to other pro-apoptotic or cell cycle regulating agents, as discussed below.

a. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

b. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

c. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with triterpenoid derivative therapy. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

d. Gene Therapy

In yet another embodiment, the secondary treatment is a secondary gene therapy in which a therapeutic polynucleotide is administered before, after, or at the same time as triterpenoid derivative. Therapeutic genes may include an antisense version of an inducer of cellular proliferation (sometimes called an oncogene), an inhibitor of cellular proliferation (sometimes called a tumor suppressor), or an inducer of programmed cell death (sometimes called a pro-apoptotic gene).

e. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

f. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adehesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

g. Anti-Inflammatory Agents

It is contemplated that other anti-inflammatory agents will be used in conjuction with the triterpenoid derivatives of the current invention. Other COX inhibitors may be used, including arylcarboxylic acids (salicylic acid, acetylsalicylic acid, diflunisal, choline magnesium trisalicylate, salicylate, benorylate, flufenamic acid, mefenamic acid, meclofenamic acid and triflumic acid), arylalkanoic acids (diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin and sulindac) and enolic acids (phenylbutazone, oxyphenbutazone, azapropazone, feprazone, piroxicam, and isoxicam. (U.S. Pat. No. 6,025,395)

Histamine H2 receptor blocking agents may also be used in conjunction with the terpenoid derivatives of the current invention, including cimetidine, ranitidine, famotidine and nizatidine.

h. Anti-Cholinesterase Inhibitors

Treatment with acetylcholinesterase inhibitors such as tacrine, donepizil, metrifonate and rivastigmine for the treatment of Alzheimers and other disease in conjunction with the triterpenoid derivatives of the present invention is contemplated. Other acetylcholinesterase inhibitors may be developed which may be used once approved include rivastigmine and metrifonate.

Acetylcholinesterase inhibitors increase the amount of neurotransmitter acetylcholine at the nerve terminal by decreasing its breakdown by the enzyme cholinesterase.

i. Estrogen Replacement Therapy

Estrogen replacement therapy (ERT) can be used in conjunction with the triterpenoid derivatives of the current invention for the treatment of Alzheimer's and other diseases. Estrogen is an excellent neuroprotective agent and effects multiple pathways that are involved in the pathogenisis of diseases that also involve excessive production of either nitric oxide (NO) or prostaglandins.

j. MAO-B Inhibitors

MAO-B Inhibitors such as selegilene (Eldepryl or Deprenyl) may be used in conjunction with the triterpenoid derivatives of the current invention. Selegilene is used for Parkinson's disease and irreversibly inhibits monoamine oxidase type B (MAO-B). Monoamine oxidase is an enzyme that inactivates the monoamine neurotransmitters norepinephrine, serotonin and dopamine.

k. Pharmaceutical Agents for MS

Common drugs for multiple sclerosis (MS) that can be used in combination with the triterpeonoid derivatives include immunosuppressive drugs such as azathioprine (Imuran), cladribine (Leustatin), and Clyclophosphamide (Cytoxan).

l. Supplements

Dietary and nutritional supplements with reported benefits for treatment or prevention of Parkinson's, Alzheimer's, multiple sclerosis, amyotropic lateral sclerosis, rheumatoid arthritis, inflammatory bowel disease, and all other diseases whose pathogenesis is believed to involve excessive production of either nitric oxide (NO) or prostaglandins, such as acetyl-L-carnitine, octacosanol, evening primrose oil, vitamin B6, tyrosine, phenylalanine, vitamin C, L-dopa, or a combination of several antioxidants may be used in conjunction with the triterpenoid derivatives of the current invention.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example I

Synthesis of New Oleanane Triterpenoids

Dinitrile 1 was synthesized from CDDO by the method as shown in Scheme 1. Oxalyl chloride gave acyl chloride 19 in quantitative yield. Amide 3 was prepared in 91% yield from 19 with ammonia gas in benzene. Dehydration of 3 with thionyl chloride gave 1 in 89% yield (Drefahl and Huneck, 1958). Ester 5 was synthesized in 83% yield from CDDO by a nucleophilic substitution method using an alkyl halide and DBU in toluene (reflux) (Ono et al., 1978) (Method A) Amides including imidazolides were synthesized in good yield by condensation reactions (Method B, scheme 1) between acyl chloride 19 and the corresponding amines and imidazoles. Tetra-O-acetyl-β-D-glucopyranoside 2 was prepared in 75% yield from tetra-O-acetyl-α-D-glucopyranoside bromide (Lemieux, 1963) and CDDO using a phase-transfer catalyst (Bliard et al., 1994) (Scheme 2) (Method C). Because in the $^1$H-NMR spectrum (300 MHz, CDCl$_3$) of 2 the anomeric proton was observed at δ 5.70 ppm (1H, d, J=7.8 Hz) the proton was assigned the β-configuration.

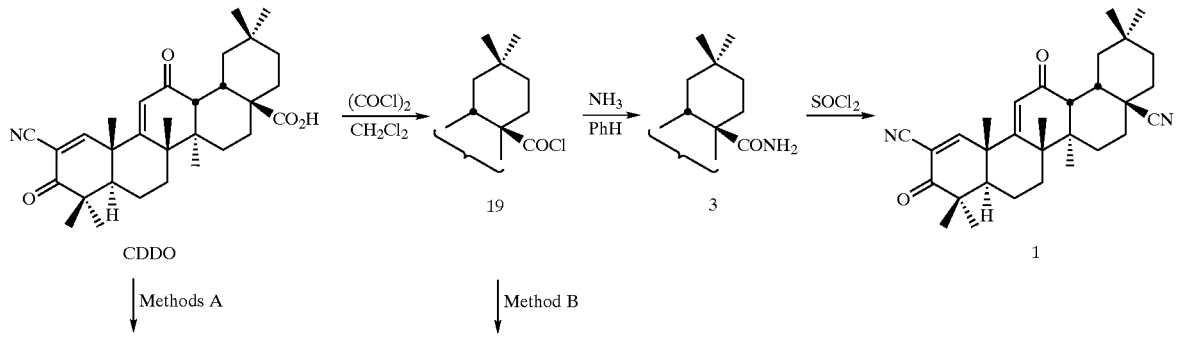

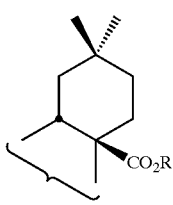
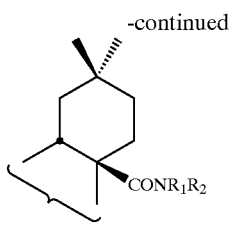

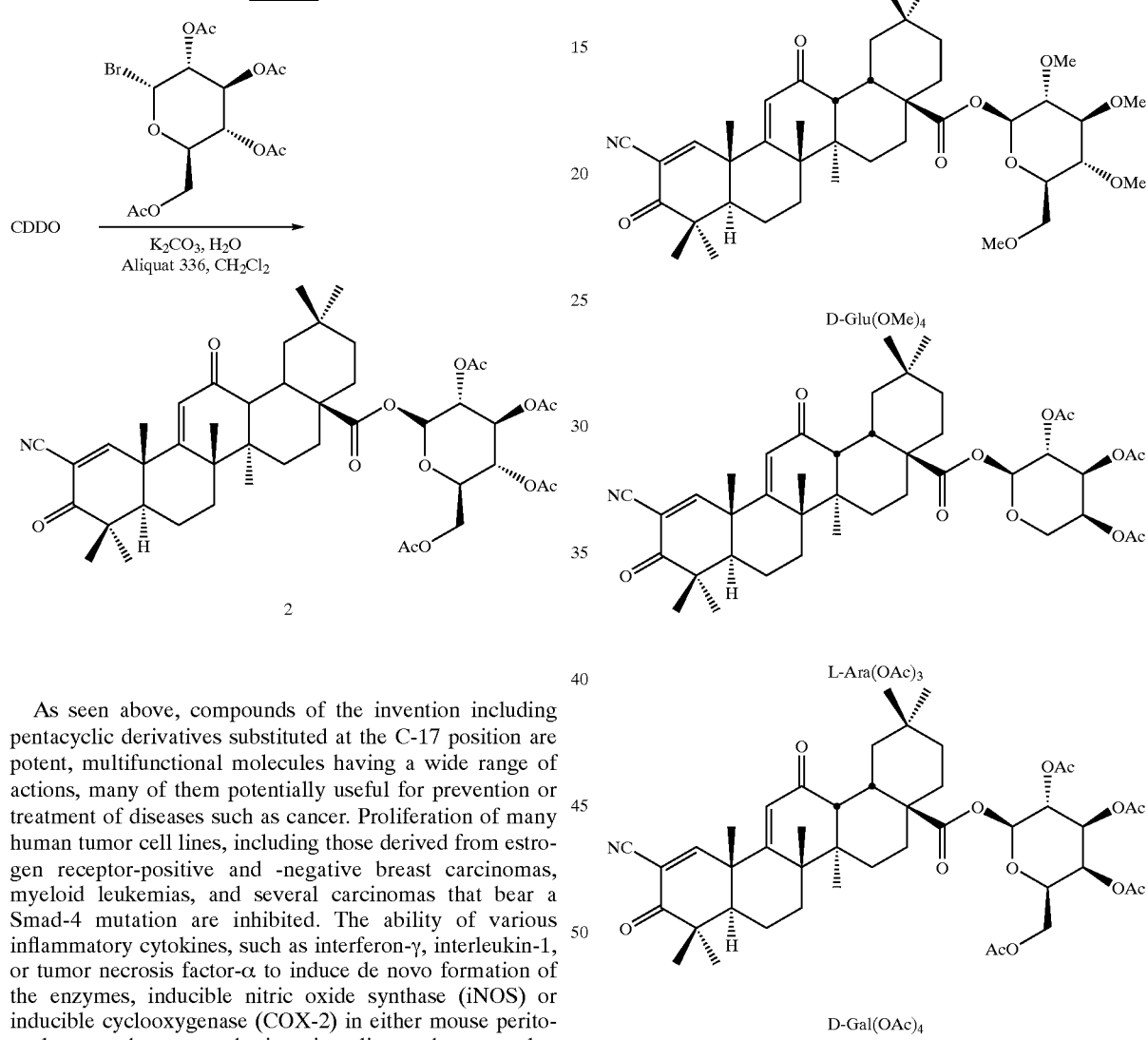

As seen above, compounds of the invention including pentacyclic derivatives substituted at the C-17 position are potent, multifunctional molecules having a wide range of actions, many of them potentially useful for prevention or treatment of diseases such as cancer. Proliferation of many human tumor cell lines, including those derived from estrogen receptor-positive and -negative breast carcinomas, myeloid leukemias, and several carcinomas that bear a Smad-4 mutation are inhibited. The ability of various inflammatory cytokines, such as interferon-γ, interleukin-1, or tumor necrosis factor-α to induce de novo formation of the enzymes, inducible nitric oxide synthase (iNOS) or inducible cyclooxygenase (COX-2) in either mouse peritoneal macrophages, rat brain microglia, or human colon fibroblasts is suppressed. Also, brain hippocampal neurons are protected from cell death induced by β-amyloid. This data indicates that the compounds of the invention are useful in vivo, both for chemoprevention or chemotherapy of malignancy, as well as for neuroprotection and for the treatment and prevention of inflammatory disorders and diseases involving iNOS and COX-2.

In addition, three other protected glycosides have also been synthesized by the methods as outlined in Scheme 2 (Method C). These compounds have the following structures:

Table 3 in Example 2 describes the potency of these three protected glycosides.

Example 2

Biological Results

The inhibitory activities [$IC_{50}$ (nM) value] of new synthetic triterpenoids 1–15, oleanolic acid, and dexamethasone on NO production induced by INF-γ in mouse macrophages are shown in Tables 1 and 2. Table 3 describes the potency of three protected glycosides synthesized namely D-Glu(OMe)$_4$,16 L-Ara(OAc)$_3$,17 and D-Gal(OAc)$_4$18 Dinitrile 1 and imidazolides 6, 9, and 10 show extremely high potency ($IC_{50}$ 0.01~3.5 pM); it is about 100–10000 times more potent than CDDO and dexamethasone.

TABLE 1

Synthesis and Biological Potency of New Oleanane Triterpenoids

| Compound | R | Method | yield (%) from CDDO | IC$_{50}$ (nM)[a] |
|---|---|---|---|---|
| 1 | CN | Scheme 1 | 81 | 0.0035 |
| 2 | CO-D-Glu(OAc)$_4$ | Scheme 2 | 75 | 0.070 |
| 3 | CONH$_2$ | Scheme 1 | 91 | 0.098 |
| 4 | CONHNH$_2$ | B | 55 | 0.26 |
| 5 | (methyl dioxolenone-CO$_2$-) | A | 62 | 0.3 |
| 6 | (imidazolyl-CO-) | B | 83 | 0.00003 |
| 7 | (benzimidazolyl-CO-) | B | 60 | 0.3 |
| 8 | (triazolyl-CO-) | B | 50 | 0.05 |
| CDDO | CO$_2$H | | | 0.44 |
| Oleanolic acid (OA) | | | | >40,000 |
| Dexamethasone | | | | 0.10 |

[a]IC$_{50}$ values of compounds 1–8 and dexamethasone were determined in the range of 0.01 pM-1 µM (10-fold dilutions). Values are an average of several separate experiments. None of the compounds were toxic to primary mouse macrophages at 1 µM

TABLE 2

Synthesis and Biological Potency of New Oleanane Triterpenoids

| Compound | R$_1$ | R$_2$ | R$_3$ | Method | Yield (%) from CDDO | IC$_{50}$ (nM)[a] |
|---|---|---|---|---|---|---|
| 9 | Me | H | H | B | 71 | 0.00001 |
| 10 | H | Me | H | B | 70 | 0.00001 |
| 11 | Et | H | H | B | 73 | 0.1 |
| 12 | n-Pr | H | H | B | 61 | 0.02 |
| 13 | Me | Me | H | B | 72 | 0.1 |
| 14 | Ph | H | H | B | 66 | 0.05 |
| 15 | H | Br | H | B | 55 | 0.03 |
| Oleanolic acid | | | | | > | 40,000 |
| Dexamethasone | | | | | | 0.10 |

[a]IC$_{50}$ values of compounds 9–15 and dexamethasone were determined in the range of 0.01 pM-1 µM (10-fold dilutions). Values are an average of several separate experiments. None of the compounds were toxic to primary mouse macrophages at 1 µM.

Compounds 1–15 exhibited satisfactory spectral data including high-resolution mass spectra and elemental analysis.

TABLE 3

Synthesis and Biological Potency of New Oleanane Triterpenoids

| Compound | R | Method | Yield (%) from CDDO | IC$_{50}$ (nM)[a] |
|---|---|---|---|---|
| 16 | CO-D-Glu(OMe)$_4$ | C | 57 | 0.300 |
| 17 | CO-L-Ara(OAc)$_3$ | C | 80 | 0.100 |
| 18 | CO-D-Gal(OAc)$_4$ | C | 77 | 0.050 |
| CDDO | | | | 0.700 |

[a]IC$_{50}$ values of these compounds were determined in the range of 0.01 pM-1 µM (10-fold dilutions). Values are an average of several separate experiments. None of the compounds were toxic to primary mouse macrophages at 1 µM.

The procedure for determining $IC_{50}$ on NO production induced by INF-γ in mouse macrophages is as follows. Macrophages were harvested from female mice injected intraperitoneally four days previously with 4% thioglycollate. These cells were seeded in 96-well tissue culture plates and incubated with 4 ng/mL INF-γ in the presence or absence of inhibitory test compounds. After 48 hours NO production, measured as nitrate by the Griess reaction, was determined. This method is described fully by Ding et al. (1990) and Bogdan and Ding, (1992).

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

REFERENCES

The following references, and those listed in the Appendix, to the extent that they provide exemplary procedural or other details supplementary to those set forth herein, are specifically incorporated herein by reference.

U.S. Pat. No. 6,025,395
U.S. Pat. No. 6,326,507
Ambs et al., *Nat. Med.*, 4(12):1371–1376, 1998.
Bagasra et al., *Proc. Natl. Acad. Sci. USA*, 92(26): 12041–12045, 1995.
Bliard, S., *Tetrahedron Lett.*, 35:6107–6108, 1994.
Bogdon and Ding, *J. Leukoc. Biol.*, 52(1):119–121, 1992.
Boolbol et al., *Cancer Res.*, 56(11):2556–2560, 1996.
Coyle and Puttfarcken, *Science*, 262(5134):689–695, 1993.
Culver et al., *Science*, 256(5063):1550–1552, 1992.
Ding et al., *J Immunol.*, 145(3):940–944, 1990.
Drefahl and Huneck, *Chem. Ber.*, 91:278–281, 1958.
DuBois et al., *Gastroenterology*, 110:1259–1262, 1996.
Genain and Hauser, J. Mol. Med., 75(3):187–197, 1997.
Honda et al., Bioorg. *Med. Chem. Lett.*, 7:1623–1628, 1997.
Honda et al., *Bioorg. Med. Chem. Lett.*, 8:2711–2714, 1998.
Honda et al., *Biorg. Med. Chem. Lett.*, 9:3429–3434, 1999.
Honda et al., *J. Med. Chem.*, 43:1866–1877, 2000a.
Honda et al., *J. Med. Chem.*, 43:4233–4246, 2000b.
Huang et al., *Cancer Res.*, 54:701–708, 1994.
Kawamori et al., *Cancer Res.*, 58(3):409–12, 1998.
Lemieux, *Methods Carbohydr. Chem.*, 2:221–222, 1963.
Marnett, *Cancer Res.*, 52(20):5575–5589, 1992.
McGeer and McGeer, *Brain Res. Brain Res. Rev.*, 21(2): 195–218, 1995.
McGeer et al., *Neurology*, 47(2):425–432, 1996.
Merrill and Beneviste, *Trends Neurosci.*, 19(8):331–338, 1996.
Moncada et al.i, *Pharmacol. Rev.*, 43:109–141, 1991.
Nathan and Xie, *Cell*, 78:915–918, 1994.
Nishino et al., *Cancer Res.*, 48:5210–5215, 1988.
Ohshima and Bartsch, *Mutat. Res.*, 305:253–264, 1994.
Ono et al., *Bull. Chem. Soc. Jpn.*, 51:2401–2404, 1978.
Oshima et al., *Cell*, 87:803–809, 1996.
Prescott and White, *Cell* (Cambridge, Mass.), 87(5), 783–786, 1996.
Reddy et al., *Cancer Res.*, 56(20):4566–4569, 1996.
Salvemini et al., *J. Clin. Invest.*, 93(5):1940–1947, 1994.
Salvemini et al., *Proc. Natl. Acad. Sci. USA*, 90(15): 7240–7244, 1993.
Sambrook et al., In: Molecular cloning, Cold Spring Harbor Laboratory Press, Cold Spring Harbor, N.Y., 2001.
Sheng et al., *J. Clin. Invest.*, 99(9):2254–2259, 1997.
Siebert and Masferrer, *Receptor*, 4(1):17–23, 1994.
Simonian and Coyle, *Annu. Rev. Pharmacol. Toxicol.*, 36:83–106, 1996.
Sporn and Roberts, *J. Cvlin. Invest.*, 78:329–332, 1986.
Stewart et al., *Neurology*, 48(3):626–632, 1997.
Strejan et al., *Cell Immunol.*, 84(1):171–184, 1984.
Suh et al., *Cancer Res.*, 59:336–341, 1999.
Takahashi et al., *Cancer Res.*, 57:1233–1237, 1997.
Tamir and Tannebaum, *Biochim. Biophys. Acta*, 1288:F31-F36, 1996.
Tsujii and DuBois, *Cell*, 83:493–501, 1995.
Tsujii et al., *Cell*, 93:705–716, 1998.
Vodovotz et al., *J. Exp. Med.*, 184(4):1425–1433, 1996.
Wang et al., *Mol. Endocrinol.*, 14:1550–1556, 2000.
Williams et al., *Clin. Neurosci.*, 2(3–4):229–245., 1994.

What is claimed is:

1. A composition of matter having the formula:

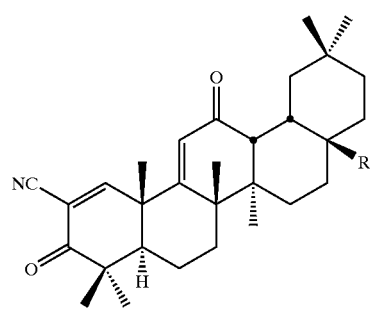

wherein, R is a substituted or unsubstituted carbonyl imidazole, CN, CO—D—Glu(OAc)$_4$, CONH$_2$, CONHNH$_2$,

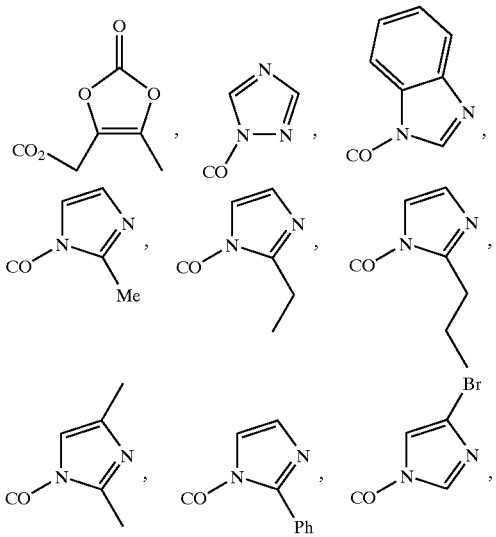

-continued

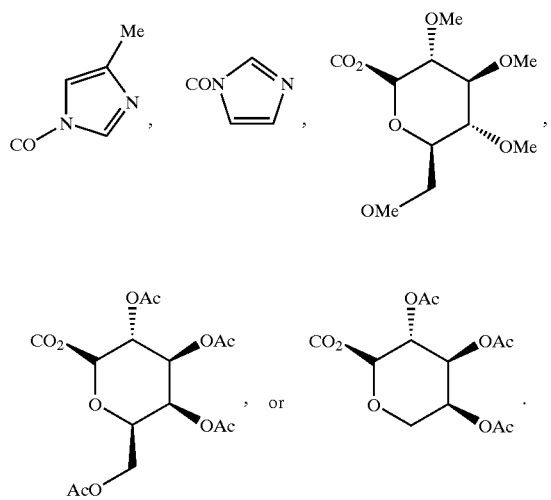

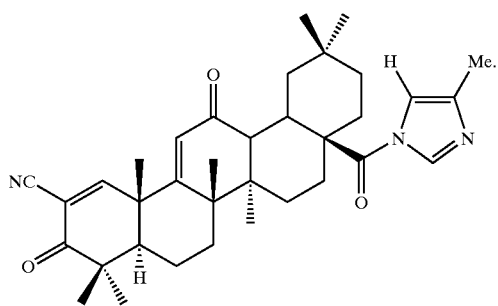

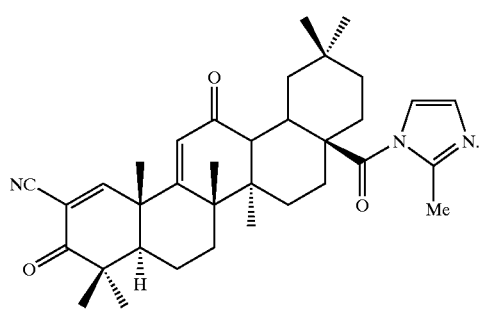

2. The composition of claim 1, wherein R is a substituted or unsubstituted carbonyl imidazole.

3. The composition of claim 1, wherein R is CN.

4. The composition of claim 1, wherein R is CO—D—Glu(OAc)$_4$.

5. The composition of claim 1, wherein R is CONH$_2$.

6. The composition of claim 1, wherein R is CONHNH$_2$ or a pharmaceutically acceptable salt thereof.

7. The composition of claim 1, wherein said composition has the formula:

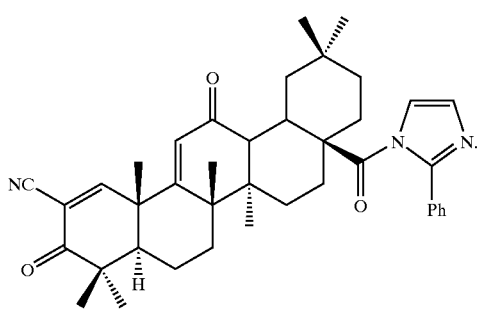

8. The composition of claim 1, wherein said composition has the formula:

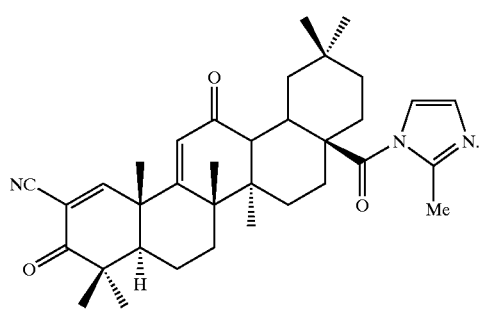

9. The composition of claim 1, wherein said composition has the formula:

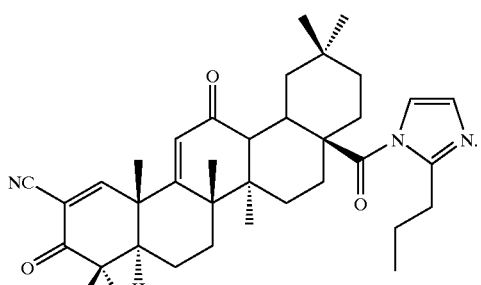

10. The composition of claim 1, wherein said composition has the formula:

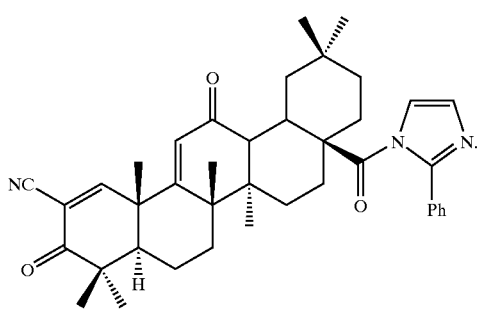

11. The composition of claim 1, wherein said composition has the formula:

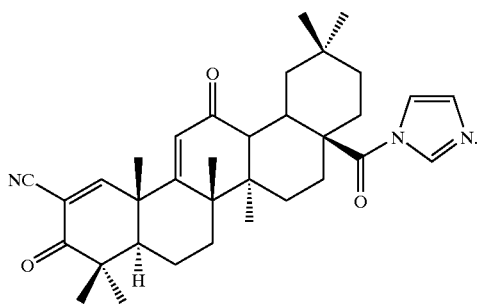

12. The composition of claim 1, wherein said composition has the formula:

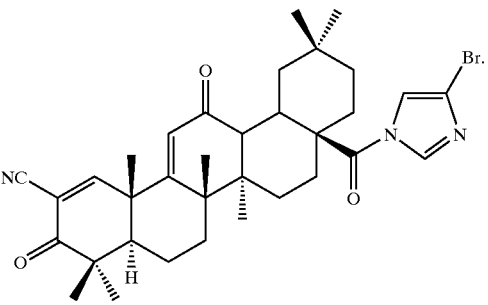

13. The composition of claim 1, wherein said composition has the formula:

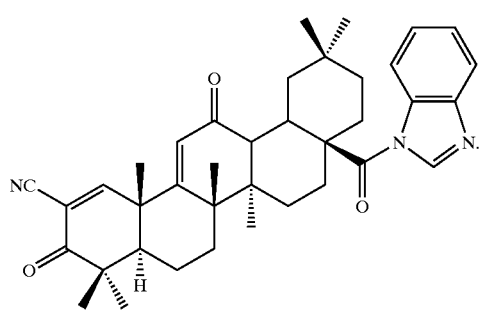

14. The composition of claim 1, wherein said composition has the formula:

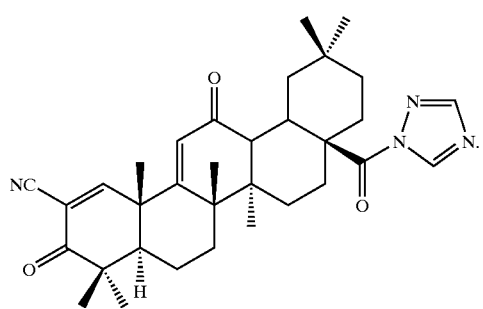

15. The composition of claim 1, wherein said composition has the formula:

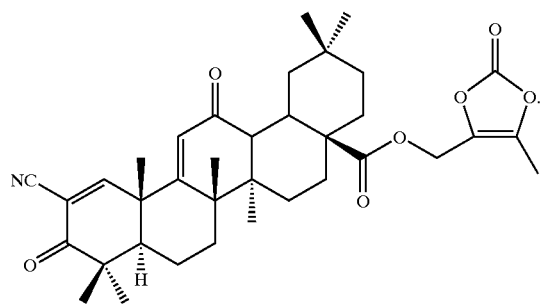

16. The composition of claim 1, wherein said composition has the formula:

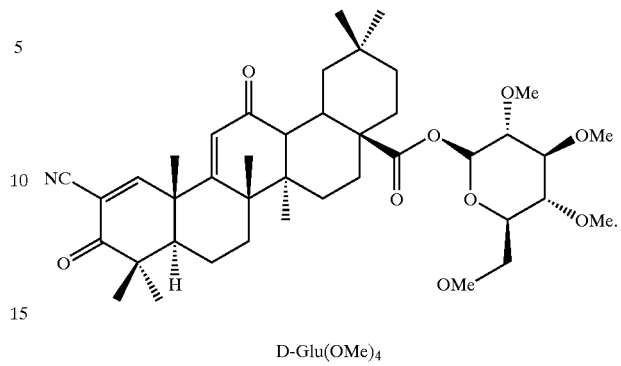

D-Glu(OMe)$_4$

17. The composition of claim 1, wherein said composition has the formula:

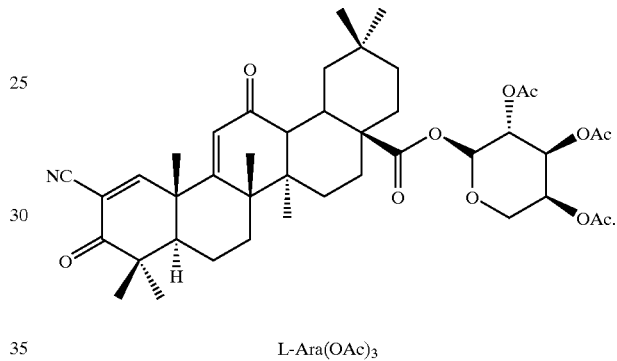

L-Ara(OAc)$_3$

18. The composition of claim 1, wherein said composition has the formula:

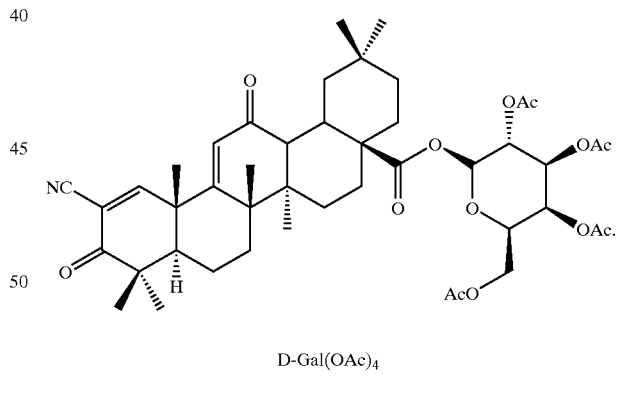

D-Gal(OAc)$_4$

\* \* \* \* \*

UNITED STATES PATENT AND TRADEMARK OFFICE
CERTIFICATE OF CORRECTION

| | |
|---|---|
| PATENT NO. | : 6,974,801 B2 |
| APPLICATION NO. | : 10/435925 |
| DATED | : December 13, 2005 |
| INVENTOR(S) | : Tadashi Honda et al. |

It is certified that error appears in the above-identified patent and that said Letters Patent is hereby corrected as shown below:

In column 1, lines 8-13, delete paragraph and insert
--This invention was made with government support under grant number 1R01-CA78814 awarded by the National Institutes of Health and grant numbers DAMD 17-96-1-6163, DAMD 17-98-1-8604, and DAMD 17-99-1-9168 awarded by the Department of Defense. The government has certain rights in the invention.-- therefor.

Signed and Sealed this
Twentieth Day of December, 2011

David J. Kappos
*Director of the United States Patent and Trademark Office*